United States Patent [19]

Brenner et al.

[11] Patent Number: 5,149,884
[45] Date of Patent: Sep. 22, 1992

[54] TUBE BUNDLE REACTOR, USE THEREOF IN EXOTHERMIC ORGANIC REACTIONS, AND PREPARATION OF KETONES AND ALDEHYDES USING SAME

[75] Inventors: Karl Brenner, Ludwigshafen; Wilhelm Ruppel, Schwetzingen; Otto Woerz, Friedelsheim; Klaus Halbritter, Mannheim; Hans-Juergen Scheiper, Mutterstadt; Werner Aquila, Mannheim; Hartwig Fuchs, Ludwigshafen, all of Fed. Rep. of Germany

[73] Assignee: BASF Aktiengesellschaft, Ludwigshafen, Fed. Rep. of Germany

[21] Appl. No.: 680,631

[22] Filed: Apr. 1, 1991

Related U.S. Application Data

[63] Continuation of Ser. No. 529,756, May 29, 1990, abandoned, and Ser. No. 399,353, Aug. 28, 1989, abandoned, and Ser. No. 34,940, Apr. 6, 1987, abandoned.

[30] Foreign Application Priority Data

Apr. 11, 1986 [DE] Fed. Rep. of Germany ....... 3612213

[51] Int. Cl.⁵ ............................................. C07C 45/39
[52] U.S. Cl. .................................. 568/471; 568/473; 568/403; 568/431; 568/320
[58] Field of Search ............... 568/471, 473, 403, 431, 568/320

[56] References Cited

U.S. PATENT DOCUMENTS 4,732,918 3/1988 Lohmueller et al. ............... 518/712

FOREIGN PATENT DOCUMENTS 0055354 7/1982 European Pat. Off. ............ 568/331
3414717 10/1985 Fed. Rep. of Germany ...... 518/712

OTHER PUBLICATIONS

Chem.-Ing.-Tech. 51 (1979), 257-265.

Primary Examiner—James H. Reamer
Attorney, Agent, or Firm—Keil & Weinkauf

[57] ABSTRACT

In a tube bundle reactor for carrying out catalytic organic reactions in the gas phase, comprising reaction tubes (A) arranged between tubesheets (B), the reaction tubes have an inside diameter ranging from 0.5 to 3 cm, the ratio of reaction tube length to inside diameter ranges from 2 to 10, and the reaction tubes (A) are surrounded by a fluid heat transport medium flowing in the crosswise direction; said tube bundle reactor is useful in particular in exothermic organic reactions.

10 Claims, 5 Drawing Sheets

FIG. 1

Reactants

Salt stream

Longitudinal flow reactor (prior art)

FIG. 2

Radial flow reactor (prior art)

Salt stream

TUBE BUNDLE REACTOR, USE THEREOF IN EXOTHERMIC ORGANIC REACTIONS, AND PREPARATION OF KETONES AND ALDEHYDES USING SAME

This application is a continuation of application Ser. No. 529,756, filed on May 29, 1990 and application Ser. No. 399,353, filed on Aug. 28, 1989 and application Ser. No. 034,940, filed Apr. 6, 1987, abandoned.

The present invention relates to a tube bundle reactor for carrying out organic reactions in the gas phase, comprising reaction tubes arranged between tubesheets; further to the use of the tube bundle reactor in exothermic organic reactions; and to a process for preparing aliphatic, aromatic or araliphatic ketones and aldehydes using the tube bundle reactor according to the invention. The tube bundle reactor according to the invention is particularly useful for carrying out catalysed reactions which are strongly exothermic and whose rate of reaction depends strongly on the temperature.

If the reactants and products are sufficiently stable, reactions of this type can be carried out adiabatically with extremely short residence times. Examples are the ammonoxidation over platinum nets and the oxidative dehydrogenation of methanol to formaldehyde over an approximately 20 mm deep damped bed of silver crystals.

If the reactants or products are unstable, so that an adiabatic process is not possible, at least part of the heat of reaction must be removed via a heat exchanger surface. The catalyst can be introduced either between (Linde's reactor: DE-A-34 14 717) or within (tube bundle reactor: Chem.-Ing.-Tech. 51 (1979), 257-265) the tubes of a heat exchanger. Reactors of this type have tubes of several centimeters in diameter and are from 2 to 20 meters in length, i.e. they have relatively long residence times. In strongly exothermic reactions a hot spot forms and frequently leads to considerable selectivity losses of or damage to the catalyst. It may be possible to remove the hot spot by diluting the catalyst with inert material at the start of the bed, or by operating with partial conversion and returning cycle gas into the reactor. This necessitates a considerable engineering outlay, namely large reactors, extensive offgas workup and the control of large amounts of cycle gas, and nonetheless it is frequently impossible to avoid selectivity losses.

Thermal instability of reactants and products coupled with a sizeable heat of reaction and a high activation energy requires a reactor which combines on the one hand the very brief residence time of the short catalyst bed adiabatic reactor and on the other at least the efficient heat removal of the tube bundle reactor.

EP-A-55 354 describes a catalytic process for the continous preparation of 3-alkylbuten-1-als by oxidative dehydrogenation of the corresponding alcohols in a tubular reactor. The tubular reactor is evidently of conventional design, nothing being said in the publication about tube dimensions or other design features, since they are evidently not critical according to existing teaching.

It is an object of the present invention to develop a tube bundle reactor of the type mentioned at the beginning in such a way that in the case of strongly exothermic reactions, in particular over extremely active catalysts, for example over noble metal catalysts, in the gas phase, proper process control is possible. In particular, reactions of this type are to be made highly selective.

We have found that this object is achieved with a tube bundle reactor of the type mentioned at the beginning, wherein the reaction tubes have an inside diameter within the range from 0.5 to 3 cm, the ratio of reaction tube length to inside diameter ranges from 2 to 10, and the reaction tubes are surrounded by a fluid heat transport medium flowing in the crosswise direction.

In a preferred embodiment, the reaction tubes have a length of from 5 to 20 cm.

Particular preference is given to a tube inside diameter of from 1 to 2 cm.

The fluid heat transport medium can be of the customary kind, molten salts being particularly preferred. The direction of flow of the fluid heat transport medium is substantially at right angles to the longitudinal axis of the particular reaction tube.

By means of the short tube bundle reactor according to the invention it is possible to obtain an extremely high and uniform flow across the tubes and hence a particularly high removal of heat. The compact design in addition permits a simple flow of the heat transport medium and leads to an inexpensive reactor having a high space-time yield. In addition, inert gas quantities which go beyond the requirements of the specific chemical process need not be supplied at all or only to a minor extent.

Whereas with existing tube bundle reactors the ratio of tube length to tube diameter ranges from 100 to 1,000, with the short tube bundle reactor according to the invention this ratio is within the range from 2 to 10. Owing to the short tubes, an industrial reactor has the shape of a flat disk of relatively low capacity. With this reactor shape, the heat transport medium need not be distributed in a large, three-dimensional space.

The present invention also provides the use of a tube bundle reactor according to the invention in exothermic organic reactions, in particular a process for preparing an aliphatic, aromatic or araliphatic ketone or aldehyde by oxidative dehydrogenation of the corresponding alcohol with a catalyst of group 1b of the periodic table. This process comprises performing the oxidative dehydrogenation in a tube bundle reactor as defined above.

A particularly advantageous embodiment of the process according to the invention is used to prepare a 3-alkylbuten-1-al of the general formula I (I)

where $R^1$ is hydrogen and $R^2$ is or $R^1$ and $R^2$ together are by passing a 3 alkylbuten-1-ol of the general formula II $$\begin{array}{c} R^1 \\ \phantom{R}\diagdown \\ \phantom{RR}CH-CH_2OH \\ \phantom{R}\diagup \\ R^2 \end{array} \quad (II)$$

where $R^1$ and $R^2$ are as defined above, together with oxygen over the catalyst at from 300° to 600° C. and, after cooling down, working up the reaction gases in a conventional manner.

Using the tube bundle reactor according to the invention, the desired products are obtained in high selectivities and conversions.

The invention and the prior art are illustrated in more detail in the drawings, where.

Figure 1:
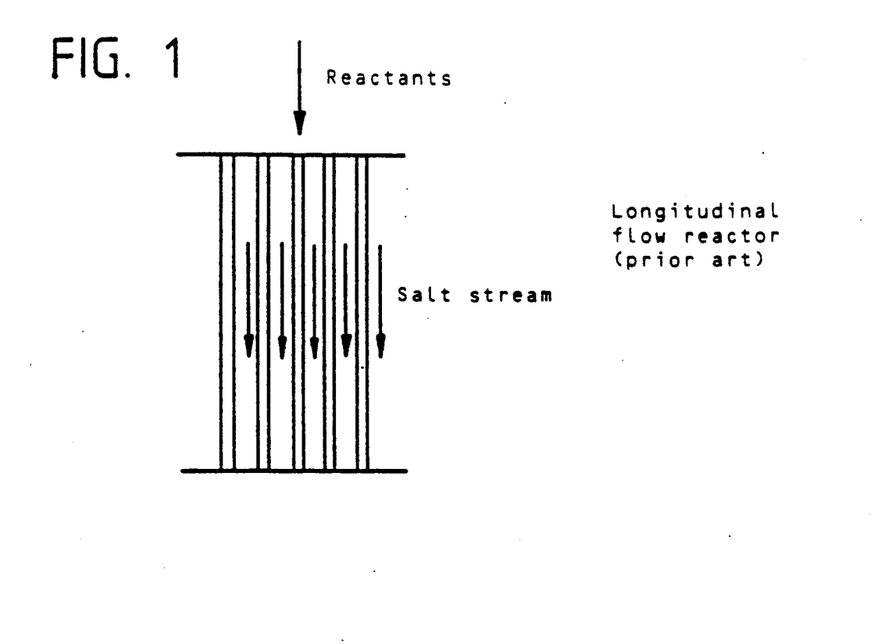
FIG. 1 shows a cross-section through a diagramatically depicted prior art longitudinal flow reactor.

In the prior art longitudinal flow reactor of FIG. 1, the reaction tubes are surrounded by a salt stream flowing uniformly and parallel to the longitudinal axis of the particular reaction tube. The disadvantage of the longitudinal flow reactor is that the salt-side heat transfer coefficient is relatively small as a consequence of the fluid heat transport medium flowing along rather than across.

Figure 2:
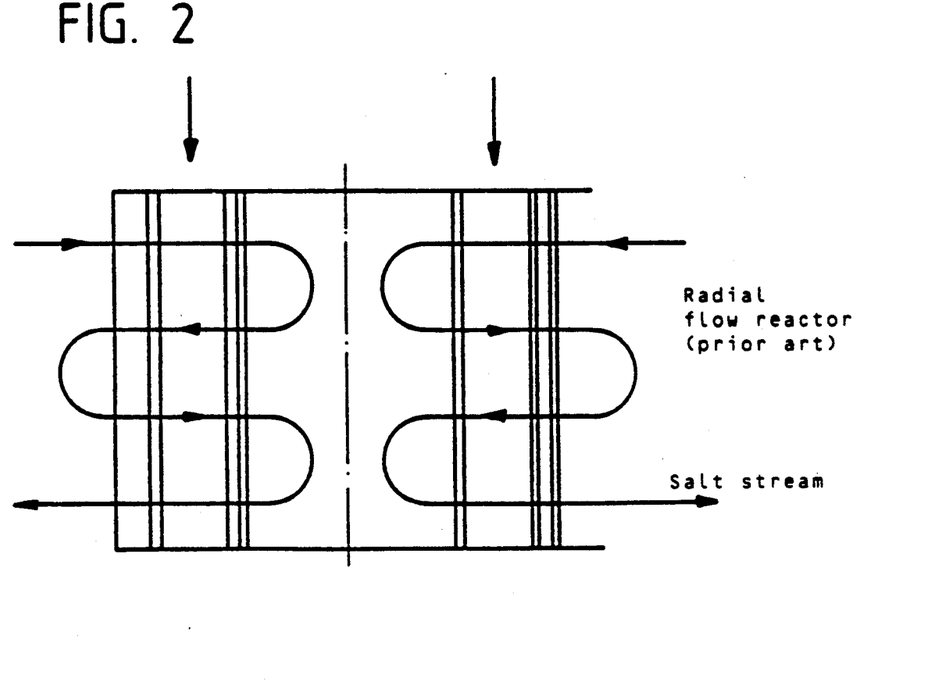
FIG. 2 shows a cross-section through a diagramatically depicted prior art radial flow reactor.

It is true that the cross-flow over the tubes in the radial flow reactor of FIG. 2 leads to a distinctly high heat transfer coefficient on the salt side, but deflections of the salt stream are necessary. To avoid nonuniform flow across the pipes, the only option is to fit out an annular space with reaction tubes.

Figure 3:
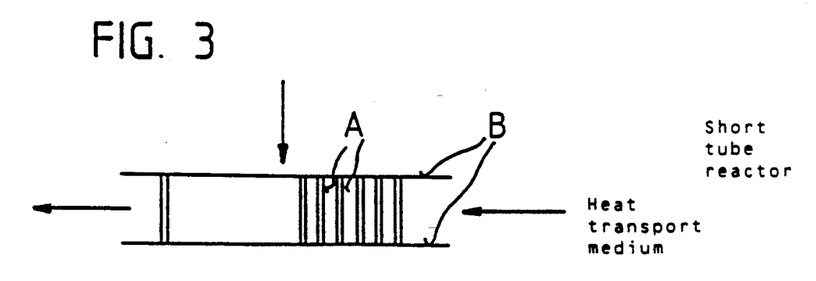
FIG. 3 shows a cross-section through a diagramatic representation of a short tube reactor according to the invention.

The short tube reactor according to the invention depicted diagramatically in FIG. 3 has a series of reaction tubes A which are fitted between two tubesheets B. A heat transport medium flows between the tubesheets B around the reaction tubes A at substantially right angles to the reaction tube longitudinal axis. The direction of flow of the heat transport medium, which preferably comprises a molten salt, is indicated in FIG. 3 by the arrows pointing toward the left. The reaction flow is indicated by the downward arrow. The reaction flow takes place through the reaction tubes. The reaction tubes are expediently arranged in a stagger.

Figure 4:
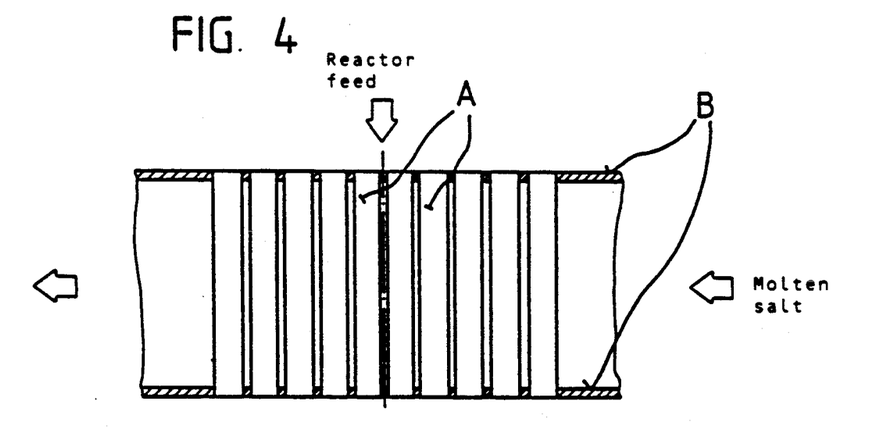
FIG. 4 shows a section of the short tube reactor of FIG. 3.
Figure 5:
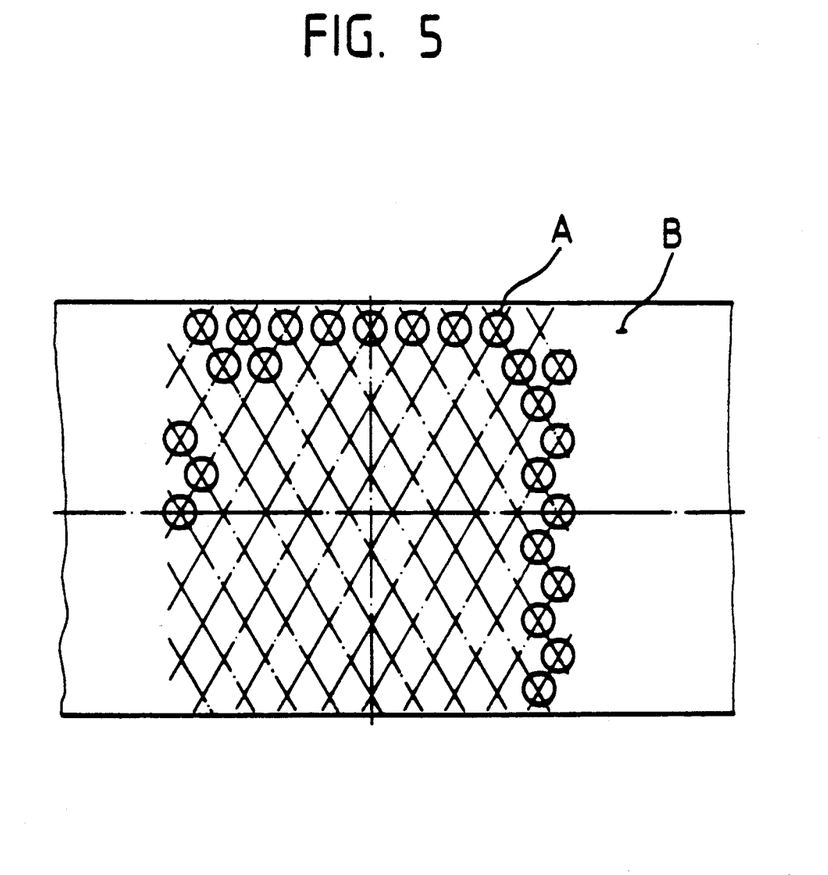
FIG. 5 shows a plan view on a part of the short tube reactor of FIG. 4.

FIG. 4 shows a detail of the short tube reactor according to the invention in section. As in FIG. 3, in FIG. 4 A signifies the reaction tubes and B the tubesheets. The embodiment depicted in FIG. 4 has a reaction tube inside diameter of preferably from 10 to 15 mm and a tube length of from preferably 50 to 200 mm. The tubes are machine welded into the tubesheets. FIG. 5 shows a tubesheet in plan view. Tubesheet B is provided with holes into which the reaction tubes are inserted. It is evident that the structure of the short tube reactor according to the invention is very simple, which has a positive effect on manufacturing costs. In particular in the case of the atmospheric pressure design, the short tube reactor has low material requirements and is particularly inexpensive to manufacture.

The heat transport medium, preferably a molten salt, flows against the reaction tubes in the transverse direction. As a result, the flow against the tubes is uniform over the tube length. As a consequence of a very high specific cooling surface area, the temperature distribution in the reaction tube can be precisely set by means of the salt temperature. It is thus always possible to obtained the maximum yield of useful product even if reactor feed composition is variable. In the case of the preferably employed noble metal catalysts, the use of inert gases can be sharply reduced.

Compared with the prior art, the tube bundle reactor according to the invention has in particular the following advantages:

1. Strongly exothermic organic reactions, preferably over noble metal catalysts, can be carried out at defined temperatures. Flexible adaptation of the reaction conditions to the particular reactants is possible.

2. The short tube reactor according to the invention permits a highly uniform cross-flow over all tubes. The result is a very compact design with maximum heat transfer coefficients.

3. Even if finely grained catalyst material is used in the reaction tubes, the pressure drop in the tubes is small. If porous catalysts are used, short diffusion paths result in a simple manner in the pores of the catalyst.

The short tube reactor according to the invention is suitable in particular for the continuous practice of catalysed reactions which are strongly exothermic and whose rate of reaction is strongly dependent upon the temperature. These reactions are for example oxidations, in particular oxidative dehydrogenations, and halogenations.

The short tube reactor is suitable in particular for preparing aliphatic, aromatic and araliphatic ketones and aldehydes by oxidative dehydrogenation of corresponding alcohols in the presence of a catalyst of group 1b of the periodic table.

Suitable starting materials are alcohols of the general formula II'

$$\begin{array}{c} R^1-CH-OH \\ | \\ R^2 \end{array} \quad (II')$$

where $R^1$ and $R^2$ are identical or different and are each hydrogen or a saturated or unsaturated, branched or unbranched aliphatic radical, preferably of 1 to 20, in particular of 1 to 12, carbon atoms, or monosubstituted or polysubstituted aryl, preferably phenyl, which, is substituted, preferably monosubstituted or disubstituted, in particular by $C_1$-$C_5$-alkyl or $C_1$-$C_5$-alkoxy, or $R^1$ and $R^2$ are each aralkyl.

Examples of possible starting material of the general formula II' are: methanol, ethanol, propanol, isopropanol, n-butanol, isobutanol, sec.-butanol, n-pentanol, 2-pentanol, 3-pentanol, 2-methylbutanol, 3-methylbutanol, hexanol, 2-hexanol, 3-hexanol, 2-methylhexanol, 3-methylhexanol, 2-ethylhexanol, heptanol, 2-heptanol, but-2-en-1-ol, but-3-en-1-ol, 2-methyl-but-3-en-1-ol, 3-methyl-but-3-en-1-ol, pent-3-en-1-ol, hex-2-en-1-ol, octen-1-en-3-ol, 2-methylbenzyl alcohol, 3-methylbenzyl alcohol, 4-methylbenzyl alcohol, 2-methoxybenzyl alcohol, 3-methoxybenzyl alcohol, 4-methoxybenzyl alcohol, 2,3-dimethylbenzyl alcohol, 3,4-dimethylbenzyl alcohol, 2,6-dimethylbenzyl alcohol, 3,5-dimethylbenzyl alcohol, 2,3-dimethoxybenzyl alcohol, 3,4-dimethoxybenzyl alcohol, 3,5-dimethoxybenzyl alcohol, 2-ethylbenzyl alcohol, 3-ethylbenzyl alcohol, 4-ethylbenzyl alcohol, 2,3-diethylbenzyl alcohol, 3,4-diethylbenzyl alcohol, 2,6-diethylbenzyl alcohol, 3,5-diethylbenzyl alcohol, 2-ethoxybenzyl alcohol, 3-ethoxybenzyl alcohol, 4-ethoxybenzyl alcohol, 2-n-propylbenzyl alcohol, 3-n-propylbenzyl alcohol, 4-n-propylbenzyl alcohol, 2,3-di-n-propylbenzyl alcohol, 3,4-di-n-propylbenzyl alcohol, 2,6-di-n-propylbenzyl alcohol, 3,5-di-n-propylbenzyl alcohol, 2-isopropylbenzyl alcohol, 3-isopropylbenzyl alcohol, 4-isopropylbenzyl alcohol, 2-butylbenzyl alcohol, 3-butylbenzyl alcohol, 4-butylbenzyl alcohol, 2-isobutylbenzyl alcohol, 3-isobutylbenzyl alcohol, 4-isobutylbenzyl alcohol, 2-tert.-butylbenzyl alcohol, 3-tert.-butylbenzyl alcohol, 4-tert.-butylbenzyl alcohol, 2,3-diethoxybenzyl alcohol, 3,4-diethoxybenzyl alcohol, 2,6-diethoxybenzyl alcohol, 3,5-diethoxybenzyl alcohol, benzylalcohol, 2,3,4-trimethoxybenzyl alcohol, 3,4,5-trimethoxybenzyl alcohol, 2,4,6-trimethoxybenzyl alcohol and corresponding trihydroxybenzyl alcohols etherified by ethyl, n-propyl, isopropyl, n-butyl, sec.-butyl, isobutyl or tert.-butyl; o-, m- or p-aminobenzyl alcohols which are unsubstituted or substituted in the above-mentioned manner and whose nitrogen atoms are disubstituted by methyl, ethyl, n-propyl, isopropyl, n-butyl, sec.-butyl, isobutyl, or tert.-butyl; o-, m- and p-hydroxymethylbenzyl alcohol and corresponding di(hydroxymethyl)benzenes which are ring-substituted in the aforementioned manner; and phenylethyl, phenylpropyl, phenylisopropyl, phenylbutyl, pheny-sec.-butyl, phenyl-tert.-butyl, phenylisobutyl, phenylpentyl, phenylhexyl and phenylisopentyl alcohols which are unsubstituted or substituted in the aforementioned manner.

For the reaction, an alcohol of the general formula II or an alcohol of the general formula II' is fed together with the solvent in vapor form and advantageously in a mixture with an inert gas into the reaction space. The solvent, which should be inert under the conditions of the reaction, is expediently tetrahydrofuran, dioxane, toluene or $H_2O$. The ratio of solvent:alcohol ranges advantageously from 0 to 1:1. The inert gas can be a noble gas but is preferably nitrogen, carbon monoxide and/or carbon dioxide. The molar ratio of inert gas:oxygen is not less than 4.4:1, expediently from 4.4 to 20:1 in each case on the basis of the total amount of, i.e. the inert gas contained in, preferably employed air.

The oxidizing agent used can not only be pure oxygen but also an oxygen-containing gas, in particular air. Oxygen, in general in the form of air, and alcohol are expediently employed in a molar ratio of from 0.1 to 0.5, in particular from 0.15 to 0.35, mole of oxygen per mole of alcohol.

The residence time of the gas mixture in the reaction space ranges from 0.0005 to 1, preferably from 0.001 to 0.05, second. Owing to the short residence time, secondary reactions are almost completely suppressed.

In the tube bundle reactor according to the invention, it is the reaction tubes which are charged with a catalyst. The thickness of the catalyst bed ranges expediently from 10 to 150 mm, preferably from 20 to 80 mm. The catalyst particles are dumped for example onto a silver or stainless steel mesh with the reactor in the upright position. Suitable catalyst articles of a particle size of from 0.1 to 5 mm.

Catalyst life with constant activity and selectivity is 3 months or more. The space velocity ranges expediently from 0.2 to 2 tonnes, in particular 0.3 to 1.5 tonnes, of alcohol per $m^2$ of catalyst cross-section per hour.

For oxidative dehydrogenation, a gas mixture of alcohol, air and inert gas is passed in the stated amounts through the catalysts at from 300° to 600° C., preferably at from 380° to 520° C. The reaction is in general carried out continuously at pressures from 0.8 to 2 bar, preferably from 1.05 to 1.5 bar.

The reaction gases leaving the reactor are rapidly cooled down to room temperature in cocurrent flow with the product mixture or with an inert solvent or with the product-containing solvent mixture and condensed. A suitable solvent is water or a solvent from the class of hydrocarbons, substituted hydrocarbons or ethers which forms two phases with water, such as hexane, toluene or methyl-tert.-butyl ether. The mixture is passed together with the reaction gases through a glass ring packed column for complete solution of the product in the solvent.

By choosing an appropriate quenching liquid, temperature and amount of quenching liquid the condensable matters can be completely recovered.

The invention is illustrated in more detail by the following Examples and Comparative Examples.

EXAMPLE 1

Preparation of 3-methyl-2-butenal

Figure 6:
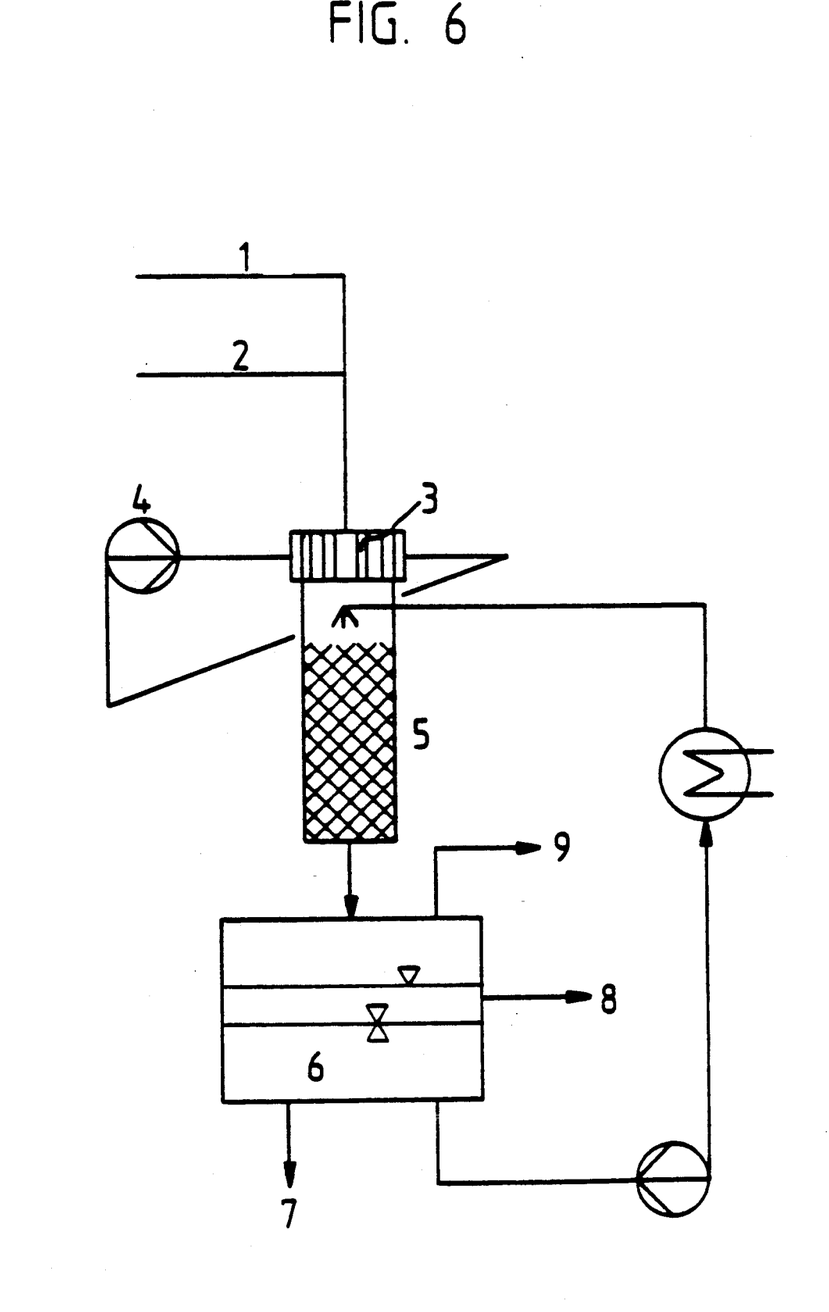
FIG. 6 shows a plant for carrying out exothermic organic reactions, in particular for the oxidative dehydrogenation of ketones and aldehydes using a tube bundle reactor according to the invention.

As depicted in FIG. 6, a plant is used with feed lines for air (1) and educt vapor (2) into a short tube bundle reactor (3). The catalyst tubes are filled to depths of 60 mm with silver catalysts of particles size 0.4–0.7 mm. The catalyst tubes are surrounded by a heat-removing stream of molten salt (4).

The hot reaction gases are quenched in a downstream column (5) which is charged with the water phase (6) of the discharged product. The two liquid phases of the discharge are removed for workup through lines (7) and (8); gaseous matters are removed by way of line (9).

The reactor is charged per hour per pipe (12 mm ID) with 44 l (S.T.P.) of air and 113 g of 3-methyl-3-buten-1-ol vapor. The temperature at the hottest spot is 420° C.

This gives, after isomerization of 3-methyl-3-butenal to 3-methyl-2-butenal, 55.8 g of 3-methyl-2-butenal and 50.9 g of unconverted 3-methyl-3-buten-1-ol, corresponding to a conversion of 55% and a selectivity of 92%.

EXAMPLE 2

Preparation of 3-methyl-2-butenal

Example 1 is repeated, except that the fine silver catalyst is replaced by a silver fraction of particle size 1.0–2.5 mm in a 100 mm deep bed. On feeding 44 l (S.T.P.) of air, 113 g of 3-methyl-3-buten-1-ol vapor and 21.5 g of steam per hour per pipe into the reactor, a maximum temperature in the catalyst of 440° C. (salt bath temperature 385° C.) gives 520 g of uncoverted 3-methyl-3-buten-1-ol and 53.6 g of 3-methyl-2-butenal, corresponding to a 3-methyl-3-buten-1-ol conversion of 54% and a selectivity of 90%.

EXAMPLE 3

Conversion of 3-methyl-2-buten-1-ol into 3-methyl-2-butenal.

Example 2 is repeated, except that the 3-methyl-3-buten-1-ol is replaced by the same amount of 3-methyl-2-buten-1-ol.

At a reaction temperature of 430° C. (salt bath temperature 380° C.) 50.2 g of unconverted 3-methyl-2-buten-1-ol and 56.6 g of 3-methyl-2-butenal are obtained, corresponding to a 3-methyl-2-buten-1-ol conversion of 55.6% and a selectivity of 92.3%.

EXAMPLE 4

The procedure of Example 1 is used to convert 3-buten-1-ol into 3-butenal in a laboratory apparatus consisting of no more than a tube cooled with a salt bath.

On feeding in 21 l (S.T.P.) of air and 56.5 g of 3-buten-1-ol per hour, 18.7 g of unconverted 3-buten-1-ol and 26.5 g of 3-butenal are obtained at a catalyst temperature of 420° C. (salt temperature 380° C.). This corresponds to a conversion of 67% and a selectivity of 72%.

EXAMPLE 5

The procedure of Example 4 is used to react 65.3 g of 4-pentan-1-ol with 20.3 l (S.T.P.) of air per hour at 440° C. (salt temperature 390° C.), giving 28.7 g of unconverted 4-penten-1-ol and 32.4 g of 4-pentenal, which corresponds to a conversion of 66% and a selectivity of 77%.

COMPARATIVE EXAMPLE 1

Preparation of 3-methyl-2-butenal in a crucible reactor (laboratory scale)

Figure 7:
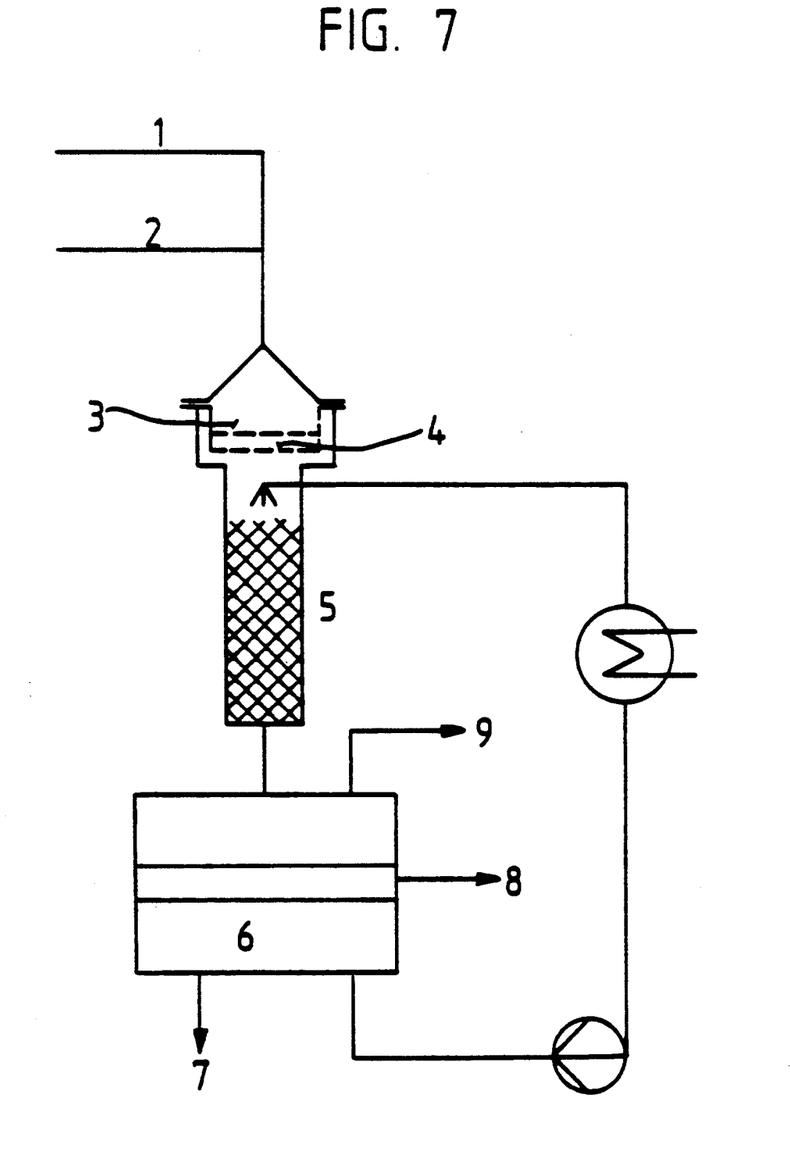
FIG. 7 shows a noninventive plant for carrying out the same reaction using a crucible reactor (Comparative Examples 1 to 4).

As depicted in FIG. 7, a plant with feed lines for air (1) and educt vapor (2) into a crucible reactor is used. The crucible has a diameter of 20 mm and contains a silver catalyst layer of the following composition (viewed in the direction of flow):

|  | Bed depth (mm) | Particle size (mm) |
| --- | --- | --- |
| Layer 1 | 10 | 0.4–0.7 |
| Layer 2 | 11 | 0.7–1.0 |

The reaction gases leaving the reactor are treated as described in Example 1.

The laboratory crucible reactor is preheated externally and then fed with 58.5 l (S.T.P.) of air and 157.1 g of 3-methyl-3-buten-1-ol vapor per hour. The temperature which becomes established on removing external heating is 495° C. Customary working up is 72.3 g of unconverted 3-methyl-3-buten-1-ol, which corresponds to a conversion of 54%, and 70.7 g of 3-methyl-2-butenal, which corresponds to a selectivity of 85.4%.

COMPARATIVE EXAMPLE 2

Preparation of 3-methyl-2-butenal in a crucible reactor (production scale)

A plant as per FIG. 7 is used, with feedlines for air (1) and educt vapor (2) into a crucible reactor (3).

The crucible has a diameter of 800 mm. The perforated floor is covered with a stainless steel mesh which supports a dumped bed of silver crystals of the following composition:

|  | Bed depth (mm) | Particle size (mm) |
| --- | --- | --- |
| Layer 1 top | 10 | 0.4–0.7 |
| Layer 2 bottom | 11 | 0.7–1.0 |

The reaction gases leaving the reactor are treated as in Example 1.

The crucible reactor is preheated with hot inert gas and then fed with 148 m³ (S.T.P.) of air and 480 kg of 3-methyl-3-buten-1-ol vapor per hour. The adiabatic temperature which becomes established is 505° C. after removal of the hot inert gases. Customary working up gives 202 kg of unconverted 3-methyl-3-buten-1-ol, which corresponds to a conversion of 57.9%, and 152 kg of 3-methyl-2-butenal, which corresponds to a selectivity of 56%.

COMPARATIVE EXAMPLE 3

A Laboratory crucible reactor as per Comparative Example 1 is used to convert 3-buten-1-ol into 3-butenal. On feeding in 55.9 L (S.T. P.) of air and 151 g of 3-buten-1-ol per hour with a reaction temperature of 510° C., 10.6 g of unconverted 3-buten-1-ol and 20.5 g of 3-butenal are recovered from the discharge, which corresponds to a 3-buten-1-ol conversion of 93% and a selectivity of 15%.

COMPARATIVE EXAMPLE 4

Comparative Example 3 is repeated to convert 4-penten-1-ol into 4-pentenal.

At a reaction temperature of 500° C., 60 L (S.T.P.) of air and 163 g of 4-penten-1-ol per hour give 40.6 g of unconverted 4-penten-1-ol and 48.9 g of 4-pentenal. This corresponds to a conversion of 75.1% and a selectivity of 40.9%.

We claim:

1. A process for the preparation of an aliphatic, aromatic or araliphatic ketone and aldehyde by oxidative dehydrogenation of the corresponding alcohol in a strong exothermic reaction with a catalyst of group 1b of the periodic table which comprises passing the alcohol to be oxidatively dehydrogenated through the tubes of a short tube bundle reactor, which contains multiple reaction tubes (A) arranged between an enclosure of tubesheets (B), and passing a fluid heat transport medium through said enclosure crosswise across said tubes (A), such that the tubes are surrounded by the heat transport medium, said transport medium providing for removal of heat from the strong exothermic reaction such that the reaction is conducted significantly isothermally wherein the reaction tubes (A) have an inside diameter of from 0.5 to 3.0 cm and the ratio of reaction tube length to inside diameter ranges from 2 to 10.

2. A process as claimed in claim 1 for preparing a 3-alkylbuten-1-al of the formula I where
R¹ is hydrogen and R² is or $R^1$ and $R^2$ are together which comprises passing a 3-alkylbuten-1-ol of the general formula II (II)

where $R^1$ and $R^2$ are as defined above, together with oxygen over a catalyst at from 300° to 600° C. and, after cooling down, working up the reaction gases in a conventional manner.

3. The process of claim 1, wherein the reaction tubes (A) have a length of from 5 to 20 cm.

4. A process as set forth in claim 3, wherein the inside diameter of the reaction tubes ranges from 1 to 2 cm.

5. A process as defined in claim 1, wherein the fluid heat transport medium is a molten salt whose direction of flow is substantially at right angles to the longitudinal axis of the particular reaction tube.

6. The process of claim 2, wherein 3-methyl-butene-1-al is prepared from 3-methyl-buten-1-ol.

7. The process of claim 2, wherein the reaction tubes have a length of from 5 to 20 cm and an inside diameter of from 1 to 2 cm.

8. The process of claim 6, wherein the reaction tubes have a length of from 5 to 20 cm and an inside diameter of from 1 to 2 cm.

9. The process of claim 2, wherein the catalyst metal is silver.

10. The process of claim 8, wherein the catalyst metal is silver.

* * * * *